(12) United States Patent
Yang et al.

(10) Patent No.: US 10,310,680 B2
(45) Date of Patent: Jun. 4, 2019

(54) DISPLAY DEVICE, HEART RATE MONITORING SYSTEM AND METHOD OF MONITORING HEART RATE

(71) Applicants: Boe Technology Group Co., Ltd., Beijing (CN); Beijing Boe Optoelectronics Technology Co., Ltd., Beijing (CN)

(72) Inventors: Jiuxia Yang, Beijing (CN); Zhidong Wang, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 41 days.

(21) Appl. No.: 15/092,834

(22) Filed: Apr. 7, 2016

(65) Prior Publication Data

US 2017/0060300 A1 Mar. 2, 2017

(30) Foreign Application Priority Data

Aug. 31, 2015 (CN) .......................... 2015 1 0545582

(51) Int. Cl.
*G06F 3/041* (2006.01)
*G06F 3/044* (2006.01)
(Continued)

(52) U.S. Cl.
CPC ............ *G06F 3/044* (2013.01); *A61B 5/0245* (2013.01); *A61B 5/044* (2013.01);
(Continued)

(58) Field of Classification Search
None
See application file for complete search history.

(56) References Cited

U.S. PATENT DOCUMENTS 5,749,367 A * 5/1998 Gamlyn ............... A61B 5/0006
600/509
2001/0031074 A1* 10/2001 Yamazaki ............... G06F 21/32
382/124

(Continued)

FOREIGN PATENT DOCUMENTS

CN 103006203 A 4/2013
CN 103271730 A 9/2013
(Continued)

OTHER PUBLICATIONS

First Office Action for Chinese Patent Application No. 201510545582.6 dated May 23, 2017.
(Continued)

*Primary Examiner* — Stephen T. Reed
(74) *Attorney, Agent, or Firm* — Calfee, Halter & Griswold LLP

(57) ABSTRACT

A display device comprising: a display module for displaying image and having a substrate being an upper component of the display module; a sensing electrode for sensing an electrocardio signal of a user, with the sensing electrode arranged above the substrate. With such a display device, high integration of the function of health test and the display device can be integrated, thereby improving usage experience of the user and facilitating to reduce the whole size of the display device.

18 Claims, 3 Drawing Sheets

(51) Int. Cl.
  *A61B 5/00* (2006.01)
  *A61B 5/04* (2006.01)
  *G06F 3/01* (2006.01)
  *A61B 5/044* (2006.01)
  *A61B 5/0245* (2006.01)
  *A61B 5/0408* (2006.01)
  *A61B 5/0428* (2006.01)
  *G02F 1/1333* (2006.01)

(52) U.S. Cl.
  CPC ........ *A61B 5/04014* (2013.01); *A61B 5/0428* (2013.01); *A61B 5/04085* (2013.01); *A61B 5/7203* (2013.01); *G02F 1/13338* (2013.01); *G06F 3/015* (2013.01); *G06F 3/0412* (2013.01); *G06F 3/0416* (2013.01); *A61B 2562/0209* (2013.01); *A61B 2562/0285* (2013.01)

(56) References Cited

U.S. PATENT DOCUMENTS

| | | | | |
|---|---|---|---|---|
| 2010/0076331 | A1* | 3/2010 | Chan | A61B 5/0006 600/522 |
| 2011/0054583 | A1* | 3/2011 | Litt | A61B 5/0031 607/116 |
| 2012/0022385 | A1* | 1/2012 | Shimuta | A61B 5/0404 600/509 |
| 2014/0333332 | A1* | 11/2014 | Matsumoto | A61B 5/6898 324/693 |
| 2016/0106320 | A1* | 4/2016 | Shimuta | A61B 5/7246 600/301 |
| 2017/0035359 | A1 | 2/2017 | Qiu et al. | |
| 2017/0045984 | A1 | 2/2017 | Lu et al. | |
| 2017/0150891 | A1* | 6/2017 | Tsuchimoto | A61B 5/02 |

FOREIGN PATENT DOCUMENTS

| | | |
|---|---|---|
| CN | 103622689 A | 3/2014 |
| CN | 104706334 A | 6/2015 |
| CN | 104716144 A | 6/2015 |
| CN | 204931663 U | 1/2016 |

OTHER PUBLICATIONS

Second Office Action for Chinese Patent Application No. 201510545582.6 dated Aug. 1, 2017.

Decision on Rejection for Chinese Patent Application No. 201510545582.6 dated Apr. 24, 2018.

Third Office Action for Chinese Patent Application No. 201510545582.6 dated Jan. 22, 2018.

* cited by examiner

DISPLAY DEVICE, HEART RATE MONITORING SYSTEM AND METHOD OF MONITORING HEART RATE

RELATED APPLICATIONS

The present application claims the benefit of Chinese Patent Application NO. 201510545582.6, filed on Aug. 31, 2015, the entire disclosure of which is incorporated herein by reference.

FIELD OF THE INVENTION

The present disclosure generally relates to the field of display technologies, and in particular, embodiments included in this disclosure relate to a display device, a heart rate monitoring system, and a method of monitoring heart rate using the display device.

BACKGROUND OF THE INVENTION

Mobile devices, such as mobile phones, are becoming more and more popular, and a variety of mobile devices have more and more powerful functions. For example, with the gradually increasing attention to the health by the human, smart mobile devices accompanying people and having a health test function are becoming popular. Mobile devices such as electronic watches, wristband, and mobile phones that are capable of measuring heartbeat the user are widely used currently. Combining a health test system with a mobile device, various body data for a user, such as body temperature, heat rate, blood velocity, oxygen saturation, or mental stress can be provided to the user. Moreover, such body data may be displayed on the mobile device, thus allowing the user to monitor his or her health status.

However, for existing mobile devices having the function of health test, the health test system is just roughly added to the original devices. For instance, an interface that can establish communication with an external health test system may be provided on the original device, such that body data measured by the external health test system can be displayed through the device. Although there may be some existing mobile devices, for which the health test function is achieved within the device, signal sensing components of the health test system are arranged outside the device. Consequently, although such mobile device is capable of testing heath status, it may still have a larger size, since the integration of the health test system and the mobile device is not really achieved. Further, usage experience for the user may be affected by such designs in which the health test system or the signal sensing components in the health test system are separated from the mobile device.

SUMMARY OF THE INVENTION

Embodiments of the invention provide an improved display device, to avoid or mitigate the problems mentioned above.

In an aspect, an embodiment of the invention provides a display device comprising a display module for displaying image and having a substrate being an upper component of the display module; and a sensing electrode for sensing an electrocardio signal of a user, the sensing electrode is arranged above the substrate.

As mentioned above, for many existing devices having the function of health test, signal sensing members of the health test system are usually arranged in an external system outside the device. Such design may increase the size of the device and affect the usage experience. With the display device provided by this embodiment of the invention, the signal sensing members may be made as a part of the display device in a real sense, and high integration of the health test system and the display device can be realized, thereby improving the user's experience, and facilitating miniaturization of the display device having the function of health test.

According to an embodiment of the invention, the sensing electrode may cover a surface of the substrate. In this case, since the sensing electrode is formed as an one-piece component covering the surface of the substrate, electrocardio signal measurement can be performed even if the user touches or clicks any position on the surface of the display device. For example, the user may touch or click the sensing electrode successively several times, then body data of the user such as a heart rate can be calculated by means of voltage differences between the sensed electrocardio signals. Thereby, this embodiment may provide a device of single point measurement.

According to another embodiment of the invention, the sensing electrode may comprise a plurality of sensing electrode units. By arranging the plurality of sensing electrode units separated from each other, it is enabled that the user touches or clicks different sensing electrode units with various body parts (e.g., fingers) simultaneously, so that body datas of the user such as a heart rate can be obtained more accurately by utilizing voltage differences between the electrocardio signals sensed from different fingers.

In an embodiment, the sensing electrode may comprise four sensing electrode units, each of which is respectively located at a corner of the surface of the display device.

In another embodiment, the sensing electrode may comprise an array of sensing electrode units, and the display device may further comprise an array of switching elements corresponding to the array of sensing electrode units, each switching element in the array of switching elements may be electrically connected with each sensing electrode unit in the array of sensing electrode units respectively. Therefore, it is enabled that the user touches or clicks different sensing electrode units with various body parts (e.g., fingers) simultaneously, so that the accuracy of electrocardio signal measurement may be improved, moreover, electrocardio signal measurement may be achieved even if the user places his or her fingers at random on any positions of the surface of the display device, which may be more convenient for the user and may further improve usage experience of the user.

According to yet another embodiment of the invention, each sensing electrode unit may be electrically connected with a source or drain of each switching element in the array of switching elements respectively. In this way, the electrocardio signal sensed by the sensing electrode units may be transferred to the controller via the switching elements, then processed and analyzed by the controller to obtain a desired body data.

According to a further embodiment of the invention, a layer of the array of the switching elements may be arranged between a layer of the sensing electrode and the substrate.

According to a further embodiment of the invention, the display device may also comprise a buffer layer between the substrate and the layer of the array of the switching elements. The substrate such as a glass substrate typically contains a metal ion, the buffer layer can prevent the metal ion originating from the substrate from permeating into the above switching elements, which is advantageous to maintain the stability of the performance of the switching elements.

According to yet another embodiment of the invention, the display device may further comprise a planarization layer covering the array of the switching elements.

According to yet another embodiment of the invention, the display device may further comprise a passivation layer formed above the planarization layer, the array of sensing electrode units may be formed above the passivation layer.

According to yet another embodiment of the invention, the display device may comprise a controller for processing and analyzing the electrocardio signal sensed by the sensing electrode, and the controller may comprise: a filtering and protection circuit for filtering out a high-frequency interference signal in the electrocardio signal received from the sensing electrode; a preamplifier for amplifying the filtered electrocardio signal; an isolating circuit for isolating an output signal of the preamplifier from post-stage circuits of the controller; a driving and amplifying circuit for amplifying an output signal from the isolating circuit; a generation circuit for generating a signal of heart rate of the user by means of the amplified signal from the driving and amplifying circuit; and an output circuit, which is used for outputting the generated signal of heart rate to show the heart rate to the user through the display device.

For the display devices as described in any one of the embodiments mentioned above, materials for forming the sensing electrode may comprise at least one selected from the group consisting of indium tin oxide, carbon nanotube and grapheme, the substrate may comprise a glass substrate.

In another aspect, an embodiment of the invention provides a heart rate monitoring system, which may comprise a display device as described in any one of the embodiments mentioned above, the heart rate monitoring can be performed through the user touching the sensing electrode of the display device with a finger.

In a further aspect, an embodiment of the invention provides a method of monitoring heart rate using a display device, the display device may comprise a display module for displaying image and having a substrate being an upper component of the display module; and a sensing electrode for sensing an electrocardio signal of a user, the sensing electrode being arranged above the substrate, the method may comprise the user touching the sensing electrode with a finger to perform heart rate monitoring.

In an embodiment, the method may further comprise steps of touching or clicking the sensing electrode successively several times, to successively obtain multiple voltage signals indicative of electrocardio signal of the user; calculating voltage differences between the obtained multiple voltage signals; and calculating a heart rate of the user by means of the voltage differences.

In another embodiment, the sensing electrode may comprise a plurality of sensing electrode units, and the method comprises steps of touching different sensing electrode units with various fingers, to obtain voltage signals indicative of electrocardio signal of the user from each of the fingers; calculating voltage differences between the voltage signals obtained from different fingers; and calculating a heart rate of the user by means of the voltage differences.

In yet another embodiment of the invention, the sensing electrode may comprise an array of sensing electrode units, and the display device may further comprise an array of switching elements corresponding to the array of the sensing electrode units, each switching element in the array of switching elements may be respectively electrically connected with each sensing electrode unit in the array of sensing electrode units, and the method may further comprise the following steps: touching the display device with several fingers, each finger contacting with multiple sensing electrode units of the array of the sensing electrode units, such that the multiple sensing electrode units of the array of the sensing electrode units sense voltage signals indicative of electrocardio signal of the user from each of the fingers; averaging the voltage signals sensed by the multiple sensing electrode units contacting with each of the fingers, to get several averaged voltage signals; calculating voltage differences between the several averaged voltage signals; and calculating a heart rate of the user by means of the voltage differences between the several averaged voltage signals.

Further, a switching element electrically connected with one or more sensing electrode units of the array of sensing electrode units is turned on in case the user's finger contacts the one or more sensing electrode units, and the switching element electrically connected with the one or more sensing electrode units is turned off in case the user's finger leaves the one or more sensing electrode units.

In yet another embodiment, the method may further comprise a step of showing a curve of heart rate or a value of heart rate to the user through the display device after the heart rate of the user is calculated.

Further, the method may further comprise the following step: providing an indication of a normal heart rate to the user by the display device in case that the curve of heart rate is continuous and regular; or else, providing an indication of an abnormal heart rate to the user by the display device.

With the embodiments provided by the invention, a sensing electrode or an array of sensing electrode units are formed above the display module of the display device, so that high integration of the health test system and the display device can be realized, thereby improving the usage experience of the user and facilitating miniaturization of the display device having a function of health test.

BRIEF DESCRIPTION OF DRAWINGS

In the following, embodiments will be described in detail with reference to the drawings by way of non-limiting examples.

DETAILED DESCRIPTION OF EMBODIMENTS

Next, embodiments will be described in detail by way of example. It should be understood that, embodiments are not limited to these examples enumerated, and other variations to the disclosed embodiments can be understood and effected by those skilled in the art in practicing the claimed invention, from a study of the drawings, the disclosure, and the appended claims. Apparently, such variations also belong to the scope of the invention.

Figure 1:
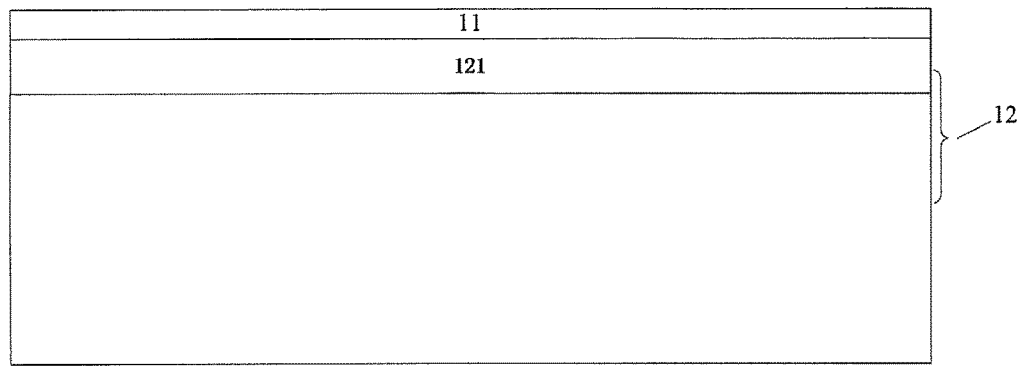
FIG. 1 schematically shows a sectional view of a display device according to an embodiment.

FIG. 1 schematically shows a sectional view of a display device according to an embodiment. As shown in FIG. 1, the display device according to this embodiment may comprise a display module 12 for displaying image and having a substrate 121 being an upper component of the display module 12, and a sensing electrode 11 for sensing an electrocardio signal of a user, the sensing electrode 11 can be arranged above the substrate 121.

The sensing electrode 11 may be made from transparent conducting materials such as indium tin oxide (ITO). Alternatively, in another embodiment, materials used for forming the sensing electrode 11 may further include other flexible materials such as carbon nanotube, graphene, etc, thereby achieving flexible display of the display device. Sensing electrodes made from such transparent materials not only can sense the electrocardio signal of the user, but also will not affect showing the image to the user by the display device. The substrate 121 being an upper component of the display module 12 can be a substrate made from an appropriate material such as glass. Thus, the substrate 121 can include but is not limited to a glass substrate.

Next, the process of electrocardio signal measurement performed by the display device provided by this embodiment will be described in detail.

As is known to a person having an ordinary skill in the art, the changes of bioelectricity of the user's heart can be reflected or embodied on the body surface of the user through conductive tissues around the heart and body fluid. Hence, various parts of the body may have a regular change of an electrical signal during each cardiac cycle. By placing a sensing electrode on the surface of a certain part of the human body, a curve of the heart's electrical signal (e.g., an electrocardiogram commonly used clinically) can be recorded.

For the display device provided with the sensing electrode according to this embodiment, the user may, for example, touch or click the sensing electrode formed on the display device with a finger. The sensing electrode may detect a voltage signal from the finger when the user's finger contacts the sensing electrode, and the voltage signal may be transferred to a controller (not shown in FIG. 1) by means of a lead wire (not shown in FIG. 1) of the sensing electrode. Therefore, the controller may process and analyze the sensed signals from the sensing electrode to obtain body data of the user. Such controller can be arranged within the display device, or alternatively, the controller can be outside of the display device. For example, if the user successively touches or clicks the sensing electrode formed on the display device two times, then voltage signals from the sensing electrode will be received successively by the controller two times. Subsequently, the controller may calculate a voltage difference between the voltage signals received at the two different times, and thereby the heart rate data of the user may be obtained by means of a conventional method of heart rate calculation. On this basis, other body data related to the user may also be obtained by utilizing various algorithms known in the art. Therefore, the display device according to this embodiment may provide a device of single point measurement for sensing electrocardio signals.

Figure 2:
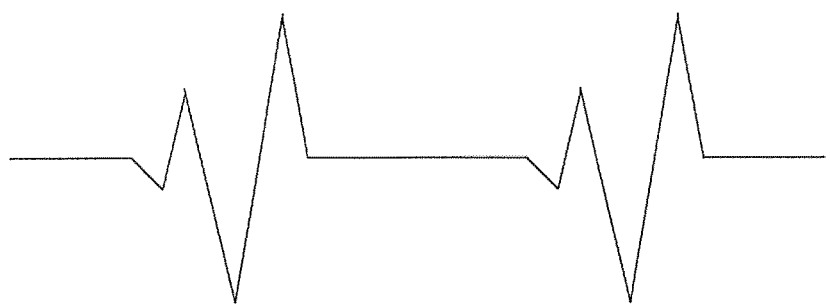
FIG. 2 schematically shows a heart rate curve displayed by a display device according to an embodiment.

Further, the heart rate tested by the display device can be shown to the user in the form of an electrocardiogram or a numerical value. After processing of the signals from the sensing electrode performed by the controller, a continuous waveform (e.g., a curve of heart rate or an electrocardiogram) can be obtained and shown to the user. For example, FIG. 2 schematically shows a heart rate curve that may be shown to the user by the display device. Alternatively, the heart rate may be calculated based on the heart rate cycle or times of peak and valley reflected by the continuous waveform, and then shown to the user in the form of a numerical value.

Further, the controller may determine whether current heart rate of the user is normal, based on the obtained curve of heart rate or value of heart rate. For example, if the resulting electrocardiogram represents a continuous and regular electrical signal, the electrocardiogram may be deemed as normal, or else, the electrocardiogram may be considered as being problematic, and indication of abnormal heartbeat may be given to the user by the display device, thus reminding the user to pay attention to the heart since there may be a problem with heart health of the user.

As mentioned above, for many existing devices having the function of health test, signal sensing members for sensing the user's electrocardio signal are usually arranged in a system outside the device, or, such signal sensing members are attached on the housing of the device simply. Consequently, such devices do not really achieve the integration of the health test system and the device, which may affect usage experience of the user and go against miniaturization for the devices. By arranging the sensing electrode above the substrate of the display module being an upper component of the display module, high integration of the function of health test and the display device can be realized, thereby improving the user's experience, and facilitating to reduce the overall size of the device.

It can be understood that the display module 12 mentioned above may be any display module known by the person having an ordinary skill in the art. In some embodiments, the display module 12 may be a liquid crystal display module. In this case, the display module 12 may comprise an array substrate, a color film substrate, and a liquid crystal layer between the array substrate and the color film substrate, and the substrate 121 may be a glass substrate of the color film substrate. Alternatively, the display module 12 may also be an organic light emitting diode (OLED) display module. In this case, the substrate 121 may be a package substrate of the OLED display module.

The sensing electrode 11 may be fabricated on the substrate 121 directly as shown in FIG. 1. In other embodiments, any proper components, such as a polarizer, may be arranged between the substrate 121 and the sensing electrode 11 as need.

In the embodiment shown in FIG. 1, the sensing electrode 11 may cover a surface of the substrate 121. Therefore, the electrocardio signal of the user may be sensed easily even if the user touches or clicks any position on the surface of the display device, which is convenient for the user.

Figure 3:
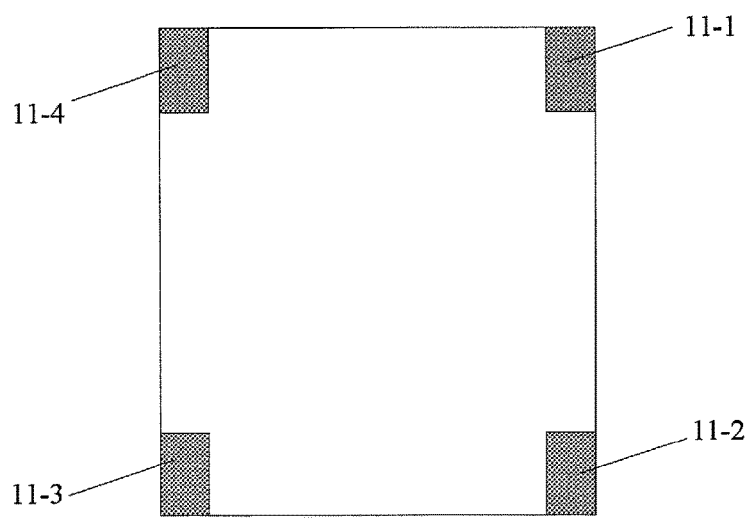
FIG. 3 schematically shows a planar top view of a display device according to another embodiment.

Alternatively, instead of being a one-piece electrode covering the substrate 121, the sensing electrode may comprise a plurality of sensing electrode units. The plurality of sensing electrode units may be arranged at one or more fixed area on the substrate 121. For example, FIG. 3 schematically shows a planar top view of a display device according to another embodiment of the invention. In this embodiment, the sensing electrode may comprise four sensing electrode units, each of which may be respectively located at a corner of the surface of the display device. For the purpose of clarity, four sensing electrode units 11-1, 11-2, 11-3 and 11-4 at the corners of the display device are predominantly shown by the shaded areas. In other embodiments, one or more sensing electrode units may be arranged at the center of the surface of display device or any positions on the surface of the display device.

By means of the sensing electrode comprising multiple sensing electrode units, the user may touch or click the sensing electrode with various body parts (e.g., fingers). For example, the user may place two fingers on different sensing electrode units, such that a heart rate data of the user can be calculated by utilizing a voltage difference between voltage signals from the two fingers. Therefore, a display device of multiple-point measurement can be provided to improve the accuracy of electrocardio signal measurement.

In another embodiment, the sensing electrode may comprise an array of sensing electrode units, the display device may also comprise an array of switching elements corresponding to the array of sensing electrode units. Each switching element in the array of switching elements may be electrically connected with each sensing electrode unit in the array of sensing electrode units respectively.

Figure 4:
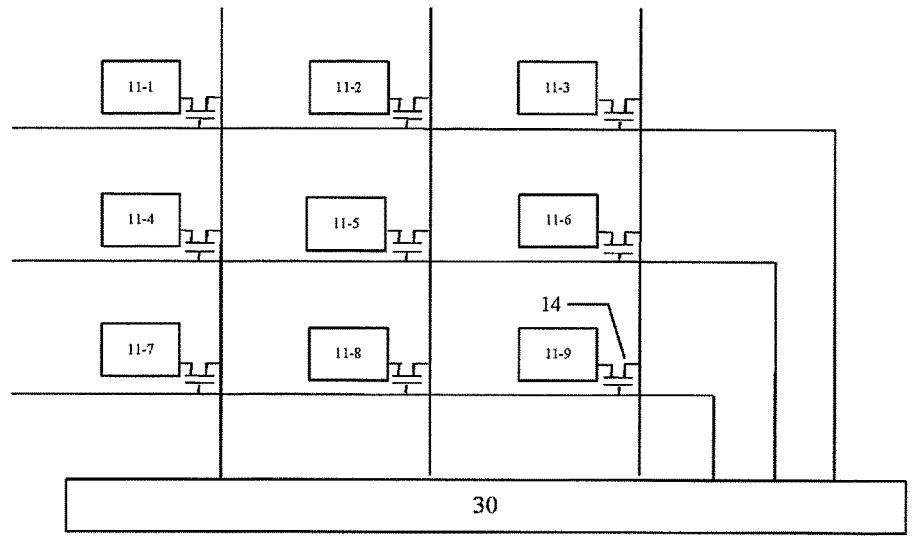
FIG. 4 schematically shows an electrical connection of a sensing electrode unit, an array of switching elements and a controller in a display device according to yet another embodiment.

FIG. 4 schematically shows an electrical connection of an array of sensing electrode units and corresponding array of switching elements, and FIG. 4 also shows a controller 30 comprised in the display device. As shown in FIG. 4, an array of sensing electrode units comprising nine sensing electrode units 11-1, 11-2, 11-3, 11-4, 11-5, 11-6, 11-7, 11-8 and 11-9 may be electrically connected with corresponding nine switching elements 14. Each sensing electrode unit may be electrically connected with the source or drain of each switching element in the array of switching elements. The controller 30 may be electrically connected with the gate of each switching element and one of the source and drain thereof in the array of switching elements, thus, the controller 30 is capable of controlling the switching elements to be on or off meanwhile, as mentioned above, process and analysis for the electrocardio signal sensed by the sensing electrode can be performed by the controller, to obtain a desired body data of the user. That is to say, in this embodiment, the functional circuit for controlling the switching elements on or off and the functional circuit for processing and analyzing the electrocardio signal sensed by the sensing electrode can be combined into one controller. Thus the whole circuit may be simplified, and the volume and size of the circuit within the display device can be reduced, which may facilitate miniaturization of the display device having the function of health test. In other embodiments, the functional circuit for controlling the switching elements on or off may also be a single circuit module.

With the display device provided by this embodiment, voltage signals from various body parts (e.g., fingers) may be sensed at the same time, so that voltage differences between these voltage signals from various body parts may be used to calculate body data, such as an electrocardiogram or a heart rate, and so on In this way, the resulting measurement will be more accurate.

For example, when the user's finger contacts a certain sensing electrode unit, the controller 30 may turn on a switching element corresponding to the sensing electrode unit, such that the electrocardio signal sensed by this sensing electrode unit may be transferred to the controller 30 via the switching element, so as to process and analyze the sensed electrocardio signal. When the finger leaves the sensing electrode unit, the controller 30 may control the corresponding switching element to be off, then controller 30 stop receiving the sensed electrocardio signal, and the function of measuring the user's electrocardio signal is disabled. In this case, the sensing electrode units may be used as measuring elements for sensing electrocardio signals of the user, and can also act as touch electrodes for detecting the touch position of the user's finger, which for example may be achieved by utilizing time division multiplexing technology known in the art. Self-capacitance detection or mutual capacitance detection, which is known to the person having ordinary skill in the art, may be utilized to determine whether the user's finger contact the sensing electrode unit and specific position of the sensing electrode unit touched by the user's finger. At this point, the sensing electrode may act as the touch electrode, and a driving signal may be applied to the sensing electrode by a touch detection chip commonly used in the art to effect touch detection. Then, the controller 30 may turn on or turn off by a corresponding switching element, depending on whether the user's finger contacts the sensing electrode unit of the display device and the specific position of the sensing electrode unit which contacts with the finger. At this moment, the driving signal applied to the sensing electrode is stopped. The sensing electrode may function as a measuring element for sensing the electrocardio signal of the user again. Related touch detection technologies are well-known for the person having ordinary skill in the art, which will not be described in detail herein.

It should be noted that the nine sensing electrode units shown in FIG. 4 are just intended to schematically show the electrical connection of the array of sensing electrode units and the array of switching elements. There may be even more than nine sensing electrode units in the array of the sensing electrode units. In some embodiments, each sensing electrode unit may be formed as an electrode block with a small size. For example, each sensing electrode unit may have a diameter of about 50 micrometers. A plurality of sensing electrode units with small sizes are arranged on the surface of the display device, therefore, body parts (e.g., fingers) of the user may contact corresponding sensing electrode units as long as the user touches any positions on the surface of the display device with his parts such as fingers. In other words, the electrocardio signal measurement can be performed even if the user places his or her fingers at random on any positions of the surface of the display device, which may further improve usage experience of the user. Moreover, when the user touches the surface of the display device with his or her hand, one body part (such as a finger) may contact or touch more than one sensing electrode units at the same time In this case, voltage signals sensed by the more than one sensing electrode units may be averaged, and similarly, voltage signals sensed by the sensing electrode units which are touched by other finger may also be averaged. Then the controller can determine the curve of heart rate or a value of heart rate based on the difference between the averaged voltage signals corresponding to different fingers. In this way, the accuracy for the electrocardio signal measurement may be further enhanced. Next, structure of a display device comprising an array of sensing electrode units and an array of switching elements will be described in detail by way of examples.

Figure 5:
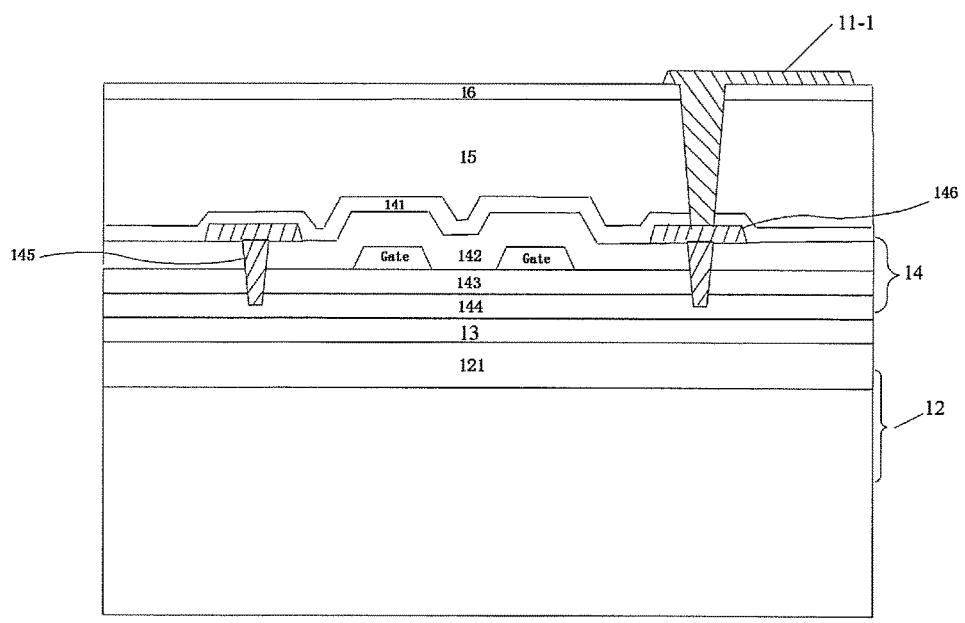
FIG. 5 schematically shows a sectional view of a display device according to yet another embodiment.

FIG. 5 schematically shows a partial sectional view of a display device according to an embodiment of the invention comprising an array of sensing electrode units and corresponding array of switching elements.

As shown in FIG. 5, the display module 12 of the display device may comprise a substrate 121 being an upper component of the display module 12. The display device further comprise a switching element 14 and a sensing electrode unit 11-1. For sake of clarity, only one switching element 14 and one sensing electrode unit 11-1 are shown in FIG. 5. The layer of the array of switching element 14 may be arranged between the layer of the sensing electrode and the substrate 121. The switching element 14 may be a thin film transistor (TFT), which may contain a channel layer 144, a gate insulation layer 143, an intermediate dielectric layer 142, a passivation layer 141, a gate, as well as a source 145 and a drain 146. The source 145 and the drain 146 may electrically connected to the channel layer 144 through a via hole, the sensing electrode unit 11-1 may electrically connected to the drain 146 through a via hole. It is noted that, in FIG. 4. To clearly illustrate the electrical connections of the sensing electrode unit 11-1, the source 145, the drain 146 with other layers, the sensing electrode unit 11-1, the source 145, the drain 146 are predominantly shown with shadow areas. It is can be understood that, the sensing electrode unit 11-1 shown in FIG. 4 is just one of the multiple sensing electrode units in the sensing electrode unit array. Alternatively, the sensing electrode unit 11-1 may be electrically connected to the source 145 of the TFT switching element 14.

In another embodiment, the display device may further comprise a buffer layer between the substrate and the layer of the switching elements. As shown in FIG. 5, the display device may further comprise a buffer layer 13 between the substrate 121 and the layer of the switching element 14. The buffer layer may be formed from oxide of silicon, so as to prevent metal ions from the substrate 121 from permeating or diffusing into the above layer of the switching elements, which may be advantageous to maintain stability of performance of the switching element 14.

As shown in FIG. 5, the display device may further comprise a planarization layer 15 covering the array of switching elements 14, which may provide a planar surface for the display device.

Further, the display device may further comprise a passivation layer 16 formed above the planarization layer 15, the array of sensing electrode blocks (units) may be formed on the passivation layer 16. The passivation layer 16 may protect the switching elements within the display device from corrosion caused by fingers of the user or the water, oxygen in the air. The sensing electrode unit 11-1 may be electrically connected to the drain or source of the switching element 14 through a via hole in the passivation layer 16 and the planarization layer 15.

Figure 6:
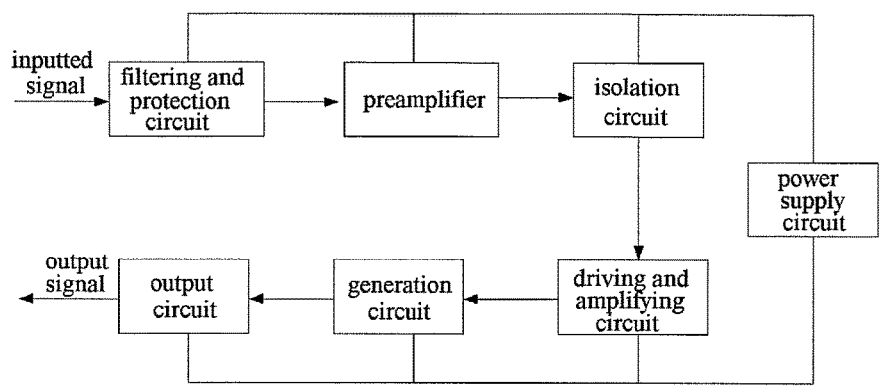
FIG. 6 schematically shows circuit modules of a controller in a display device according to an embodiment.

The controller for processing and analyzing the electrocardio signal sensed by the sensing electrode may be arranged within the display device. FIG. 6 schematically shows circuit modules of a controller in a display device according to an embodiment of the invention. The controller may comprise: a filtering and protection circuit used for filtering out a high-frequency interference signal in the electrocardio signal received from the sensing electrode; a preamplifier used for amplifying the filtered electrocardio signal; an isolating circuit used for isolating an output signal of the preamplifier from post-stage circuits of the controller; a driving and amplifying circuit for amplifying an output signal from the isolating circuit; a generation circuit for generating a signal of heart rate of the user by means of the amplified signal from driving and amplifying circuit; and an output circuit for outputting the generated signal of heart rate of the user to show the heart rate to the user through the display device.

The filtering and protection circuit may be consist of a RC low passing filter, which may only pass signals of a few tens of Hertz. The preamplifier may be a field-effect transistor constant current source differential amplifier having characteristics of high input resistance, low noise and high common mode rejection ratio, so that the received weak electrocardio signal may be amplified, and the preamplifier may have sufficient ability to suppress interference signals. The isolation circuit may comprise an optical coupling circuit, which may isolate the input of the controller coupled to the user and pre-stage circuits from the post-stage circuits of the controller, so as to prevent from a micro electrical shock and reduce the interference and affection for the post-stage circuits by the pre-stage circuits. The driving and amplifying circuit may comprise a power amplifier to amplify the output signal from the isolation circuit, to facilitate the signal processing of the generation circuit. The generation circuit may comprise an A/D conversion circuit for sampling the signals from the driving and amplifying circuit, and a processing circuit for operating or processing the sampled signals to obtain a desired body data (e.g., a heart rate value or an electrocardiogram) of the user. It can be understood by the person having an ordinary skill in the art that such processing circuit may be implemented with a dedicated chip or software programming using some known algorithms. The output circuit may comprise a D/A conversion circuit and a signal smoothing circuit, etc.

The controller shown in FIG. 6 may further comprise a power supply circuit, which may provide a proper source voltage for the filtering and protection circuit, the preamplifier, the isolation circuit, the driving and amplifying circuit, the generation circuit and the output circuit mentioned above.

The display devices provided by the above embodiments of the invention may be any device or apparatus having function of displaying. For example, the display device may be a mobile phone, a note computer, a tablet computer, etc. Therefore, by arranging the sensing electrode above the surface of the display module of the display device, the resulting display device may effect high integration of the health test system and the display device, thereby improving the user's experience, and facilitating to reduce the overall size of the device having a function of health test.

A further embodiment of the invention provides a heart rate monitoring system, which may comprise the display device as described in any one of the above embodiments, and heart rate monitoring may be achieved through the user touching the sensing electrode of the display device with a finger.

Yet another embodiment of the invention provides a method of monitoring heart rate using a display device. The display device may comprise a display module for displaying image and having a substrate being an upper component of the display module, and a sensing electrode for sensing an electrocardio signal of a user, the sensing electrode being arranged above the substrate. The method may comprise the user touching the sensing electrode with a finger to perform heart rate monitoring. Since the sensing electrode is formed above the substrate being an upper component of the display module, high integration of the function of health test and the display device can be achieved Thus, the user can perform heart rate monitoring easily and pleasantly, thereby improving the user's experience.

In some embodiments, the method may further comprise the following steps: touching or clicking the sensing electrode successively several times, to successively obtain multiple voltage signals indicative of electrocardio signal of the user; calculating voltage differences between the obtained multiple voltage signals; calculating a heart rate of the user by means of the voltage differences. As mentioned above, such method may provide a way of sensing electrocardio signal in the form of single point measurement, which is convenient to perform.

In another embodiment, the sensing electrode may comprise a plurality of sensing electrode units, and the method may comprise steps as follows: touching different sensing electrode units with various fingers, to obtain voltage signals indicative of electrocardio signal of the user from each of the fingers; calculating voltage differences between the voltage signals obtained from different fingers; calculating a heart rate of the user by means of the voltage differences. The method of this embodiment may provide a way of sensing electrocardio signal in the form of multiple-point measurement, which may help to enhance the accuracy for sensing electrocardio signal.

In a further embodiment, the sensing electrode may comprise an array of sensing electrode units, and the display device may further comprise an array of switching elements corresponding to the array of the sensing electrode units. Each switching element in the array of switching elements may be respectively electrically connected with each sensing electrode unit in the array of sensing electrode units. The method may further comprise the following steps: touching the display device with several fingers, each finger contacting with multiple sensing electrode units of the array of the sensing electrode units, such that the multiple sensing electrode units of the array of the sensing electrode units sense voltage signals indicative of electrocardio signal of the user from each of the fingers; averaging the voltage signals sensed by the multiple sensing electrode units contacting with each of the fingers, to get several averaged voltage signals; calculating voltage differences between the several averaged voltage signals; and calculating a heart rate of the user by means of the voltage differences between the several averaged voltage signals. In this way, not only a heart rate monitoring in the form of multiple-point sensing can be realized, but also the accuracy of the electrocardio signal measurement may be further improved due to the averaging for the multiple voltage signals from the same finger.

Further, when the user's finger contacts one or more sensing electrode units of the array of sensing electrode units, switching elements electrically connected with the one or more sensing electrode units may be turned on, when the user's finger leaves the one or more sensing electrode units, the switching element electrically connected with the one or more sensing electrode units may be turned off. With such controlling manner, enablement and disablement for the function of electrocardio signal measurement of the display device may be achieved. For example, when the switching element electrically connected with the one or more sensing electrode units is on, the electrocardio signal sensed by the sensing electrode units may be transferred to the controller via the switching element, such that the sensed electrocardio signal can be processed and analyzed. When the switching element is off, the controller stop receiving the sensed electrocardio signal, and the function of electrocardio signal measurement can be disabled.

In yet further embodiment, the method may further comprise a step of showing a curve of heart rate or a value of heart rate to the user by the display device after the heart rate of the user is calculated. It should be understood by the person having ordinary skill in the art, as mentioned above, the curve of heart rate or the value of heart rate for the user may be calculated by the controller within the display device using some conventional algorithms in the art for processing the sensed electrocardio signal, such algorithms are well known in the art and will not be described in detail herein.

Further, the method may further comprise the following steps: providing an indication of a normal heart rate to the user by the display device in case that the curve of heart rate is continuous and regular; or else, providing an indication of an abnormal heart rate to the user by the display device. Thus, the health status may be monitored dynamically for the user.

It is noted that, the above embodiments of the invention are intended to illustrate the principle of the invention, rather than limiting the invention. Many alternative embodiments can by effected by the person having ordinary skill in the art without departing the scope of the appended claims. In the claims, the word "comprising" does not exclude other elements or steps, and the indefinite article "a" and "an" does not exclude a plurality. The mere fact that certain measures are recited in mutually different dependent claims does not indicate that a combination of these measures cannot be used to advantage.

The invention claimed is:

1. A touch display device, comprising,
   a display module for displaying image and having a substrate being an upper component of the display module; and
   a sensing electrode for sensing an electrocardio signal of a user;
   wherein the sensing electrode is arranged above the substrate,
   wherein the sensing electrode comprises an array of sensing electrode units, and the touch display device further comprises an array of switching elements, each switching element of the array of switching elements corresponds to and is electrically connected with each sensing electrode unit of the array of sensing electrode units,
   wherein each switching element of the array of switching elements is configured to be turned on in response to a finger of the user touches the sensing electrode unit corresponding to the switching element, and turned off in response to the finger of the user leaves the sensing electrode unit corresponding to the switching element,
   wherein the array of sensing electrode units acts as touch electrodes during a touch period for detecting a touch position of the finger of the user.

2. The touch display device according to claim 1, wherein the sensing electrode covers a surface of the substrate.

3. The touch display device according to claim 1, wherein the sensing electrode comprises four sensing electrode units, each of which is respectively located at a corner of the surface of the touch display device.

4. The touch display device according to claim 1, wherein each sensing electrode unit is electrically connected with a source or drain of each switching element in the array of switching elements respectively.

5. The touch display device according to claim 4, wherein a layer of the array of the switching elements is arranged between a layer of the sensing electrode and the substrate.

6. The touch display device according to claim 5, wherein the touch display device further comprises a buffer layer between the substrate and the layer of the array of the switching elements.

7. The touch display device according to claim 6, wherein the touch display device further comprises a planarization layer covering the array of the switching elements.

8. The touch display device according to claim 7, wherein the touch display device further comprises a passivation layer formed above the planarization layer, and wherein the array of sensing electrode units is formed above the passivation layer.

9. The touch display device according to claim 8, wherein the touch display device comprises a processor for processing and analyzing the electrocardio signal sensed by the sensing electrode, and each switching element of the array of switching elements is configured to control an electrical connection between a corresponding sensing electrode unit and the processor, wherein the processor comprises:
- a filtering and protection circuit for filtering out a high-frequency interference signal in the electrocardio signal received from the sensing electrode;
- a preamplifier for amplifying the filtered electrocardio signal;
- an isolating circuit for isolating an output signal of the preamplifier from post-stage circuits of the processor;
- a driving and amplifying circuit for amplifying an output signal from the isolating circuit;
- a generation circuit for generating a signal of heart rate of the user by means of the amplified signal from the driving and amplifying circuit; and
- an output circuit, which is used for outputting the generated signal of heart rate to show the heart rate to the user through the touch display device.

10. The touch display device according to claim 1, wherein materials for forming the sensing electrode comprise at least one selected from the group consisting of indium tin oxide, carbon nanotube, and graphene.

11. The touch display device according to claim 1, wherein the substrate comprises a glass substrate.

12. A heart rate monitoring system comprising a touch display device, the touch display device comprising:
- a display module for displaying image and having a substrate being an upper component of the display module;
- a sensing electrode for sensing an electrocardio signal of a user, the sensing electrode being arranged above the substrate,
- wherein the heart rate monitoring is performed through the user touching the sensing electrode of the touch display device with a finger,
- wherein the sensing electrode comprises an array of sensing electrode units, and the touch display device further comprises an array of switching elements, each switching element of the array of switching elements corresponds to and is electrically connected with each sensing electrode unit of the array of sensing electrode units,
- wherein each switching element of the array of switching elements is configured to be turned on in response to a finger of the user touches the sensing electrode unit corresponding to the switching element, and turned off in response to the finger of the user leaves the sensing electrode unit corresponding to the switching element,
- wherein the array of sensing electrode units acts as touch electrodes during a touch period for detecting a touch position of the finger of the user.

13. A method of monitoring heart rate using a touch display device, the touch display device comprising:
- a display module for displaying an image and having a substrate being an upper component of the display module; and
- a sensing electrode for sensing an electrocardiosignal of a user, the sensing electrode being arranged above the substrate,
- wherein the sensing electrode comprises an array of sensing electrode units, and the touch display device further comprises an array of switching elements, each switching element of the array of switching elements corresponds to and is electrically connected with each sensing electrode unit of the array of sensing electrode units,
- wherein each switching element of the array of switching elements is configured to be turned on in response to a finger of the user touches the sensing electrode unit corresponding to the switching element, and turned off in response to the finger of the user leaves the sensing electrode unit corresponding to the switching element,
- wherein the array of sensing electrode units acts as touch electrodes during a touch period for detecting a touch position of the finger of the user,
- wherein the method comprises the user touching the sensing electrode with a finger to perform heart rate monitoring.

14. The method according to the claim 13, wherein the method further comprises steps of:
- touching or clicking the sensing electrode successively a plurality of times to successively obtain multiple voltage signals indicative of electrocardio signal of the user;
- calculating voltage differences between the obtained multiple voltage signals; and
- calculating a heart rate of the user by means of the voltage differences.

15. The method according to the claim 13, wherein the sensing electrode comprises a plurality of sensing electrode units, and wherein the method comprises steps of:
- touching different sensing electrode units with various fingers, to obtain voltage signals indicative of electrocardio signal of the user from each of the fingers;
- calculating voltage differences between the voltage signals obtained from different fingers; and
- calculating a heart rate of the user by means of the voltage differences.

16. The method according to the claim 15, wherein method further comprises steps of:
- touching the touch display device with several fingers, each finger contacting with multiple sensing electrode units of the array of the sensing electrode units such that the multiple sensing electrode units of the array of the sensing electrode units sense voltage signals indicative of electrocardio signal of the user from each of the fingers;
- averaging the voltage signals sensed by the multiple sensing electrode units contacting with each of the fingers to get a plurality of averaged voltage signals;
- calculating voltage differences between the plurality of averaged voltage signals; and
- calculating a heart rate of the user by means of the voltage differences between the plurality of averaged voltage signals.

17. The method according to the claim 16, wherein a switching element electrically connected with one or more sensing electrode units of the array of sensing electrode units is turned on in case the user's finger contacts the one or more sensing electrode units,
and the switching element electrically connected with the one or more sensing electrode units is turned off in case the user's finger leaves the one or more sensing electrode units.

18. The method according to the claim 13, the method further comprises a step of showing a curve of heart rate or a value of heart rate to the user through the touch display device after the heart rate of the user is calculated.

* * * * *